(12) United States Patent
Shen et al.

(10) Patent No.: US 8,778,401 B2
(45) Date of Patent: Jul. 15, 2014

(54) MESOPOROUS MATERIAL EXCIPIENTS FOR POORLY AQUEOUS SOLUBLE INGREDIENTS

(75) Inventors: Shou-Cang Shen, Jurong Island (SG); Wai Kiong Ng, Jurong Island (SG); Leonard Chia, Jurong Island (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/126,160

(22) PCT Filed: Feb. 18, 2009

(86) PCT No.: PCT/SG2009/000053
§ 371 (c)(1),
(2), (4) Date: Apr. 26, 2011

(87) PCT Pub. No.: WO2010/050897
PCT Pub. Date: May 6, 2010

(65) Prior Publication Data
US 2011/0244002 A1    Oct. 6, 2011

Related U.S. Application Data

(60) Provisional application No. 61/109,016, filed on Oct. 28, 2008.

(51) Int. Cl.
  *A61K 9/14*    (2006.01)
  *A61K 9/50*    (2006.01)
  *C01B 33/00*   (2006.01)
  *C01B 33/113*  (2006.01)

(52) U.S. Cl.
  USPC ........... 424/489; 424/400; 514/543; 514/570; 977/814

(58) Field of Classification Search
  None
  See application file for complete search history.

(56) References Cited

U.S. PATENT DOCUMENTS

| | | | |
|---|---|---|---|
| 6,197,349 B1 | 3/2001 | Westesen et al. | |
| 6,653,319 B1 | 11/2003 | Xiang et al. | |
| 2002/0164380 A1 | 11/2002 | Ma et al. | |
| 2002/0197206 A1 | 12/2002 | Balkus et al. | |
| 2005/0048116 A1 | 3/2005 | Straub et al. | |
| 2006/0134219 A1* | 6/2006 | Martens et al. | 424/489 |

FOREIGN PATENT DOCUMENTS

| | | |
|---|---|---|
| EP | 1 852 393 A1 | 11/2007 |
| WO | WO 98/24724 A1 | 6/1998 |
| WO | WO 2005/082277 A1 | 9/2005 |
| WO | WO 2005/110592 A1 | 11/2005 |

OTHER PUBLICATIONS

S Shen, PS Chow, F Chen, RGH Tan. "Submicron Particles of SBA-15 Modified with MgO as Carriers for Controlled Drug Delivery." Chem. Pharm. Bull., vol. 55(7), 2007, pp. 985-991, Jul. 2007.*
G Cavallaro, P Pierro, FS Palumbo, F Testa, L Pasqua, R Aiello. "Drug Delivery Devices Based on Mesoporous Silicate." Drug Delivery, vol. 11, 2004, pp. 41-46.*
International Search Report issued in connection with corresponding International Application No. PCT/SG2009/000053, mailed May 4, 2009, 4 pages.
European Search Report issued in connection with corresponding European Application No. 09823913.0, mailed Sep. 25, 2013, 3 pages.
Heikkila, T. et al., "Evaluation of Mesoporous TCPSi, MCM-41, SBA-15, and TUD-1 Materials as API Carriers for Oral Drug Delivery," Drug Delivery vol. 14, 2007, pp. 337-347.
"Why Amorphous Drugs," Retrieved from the Internet on Apr. 21, 2009, http://www.activery.com/amorphous-drugs-and-amorphization/why-amorphous-drugs.htm publication date unknown.
Tian, R. et al., "Large-pore Mesoporous SBA-15 Silica Particles with Submicrometer Size as Stationary Phases for High-speed CEC Separation," Electrophoresis vol. 27, No. 4, 2006, pp. 742-748.
Lensveld, D.: "On the Preparation and Characterisation of MCM-41 Supported Heterogeneous Nickel and Molybdenum Catalysts," Thesis Submitted May 27, 2003 at Universiteit Utrecht, Netherlands, Retrieved from the Internet on Apr. 21, 2009, http://igitur-archive.library.uu.nl/dissertations/2003-0325-143241/inhoud.htm, publication date May 27, 2003, abstract only.
Cavallaro, G et al., "Delivery Devices Based on Mesoporous Silicate," Drug Delivery vol. 11, 2004, pp. 41-46.
Prestidge, C.A. et al., "Mesoporous Silicon: A Platform for the Delivery of Therapeutics," Expert Opinion in Drug Delivery vol. 4, No. 2, 2007, pp. 101-110.
Salonen, J. et al., "Mesoporous Silicon Microparticles for Oral Drug Delivery: Loading and Release of Five Model Drugs," Journal of Controlled Release vol. 108, 2005, pp. 362-374.
Jinno, J. et al., "Effect of particle size reduction on dissolution and oral absorption of a poorly water-soluble drug, cilostazol, in beagle dogs," Journal of Controlled Release vol. 111, 2006, pp. 56-64.
Palmiere, G.F. et al., "Inclusion complexation of fenofibrate with β-cyclodextrin and hydroxypropyl-β- cyclodextrin; evaluation of interactions in solution and solid complex characterization," STP Pharma Science vol. 7, 1997, pp. 174-181.

* cited by examiner

*Primary Examiner* — Frederick Krass
*Assistant Examiner* — Isaac Shomer
(74) *Attorney, Agent, or Firm* — Kilpatrick Townsend & Stockton, LLP

(57) ABSTRACT

The present invention encompasses formulations and methods for producing solid dispersions comprising mesoporous materials with poorly aqueous soluble active ingredients. The active ingredient is formed in the amorphous state and entrapped in the nanosized pores of the mesoporous excipients using a co-spray drying process. The pore walls of mesoporous channels stabilize the amorphous form of active ingredient against re-crystallization. The amorphous active ingredient entrapped in mesoporous channels exhibits good stability during extended storage under stress test conditions and possesses significantly enhanced dissolution rates.

28 Claims, 25 Drawing Sheets

Storage condition: 40°C/RH75% (USP standard)
Results: amorphous form remains stable for 1 year TABLET form; in 900 ml 0.1N HCl, 37°C/100 rpm IBU/SBA-15 spray dry: 50 mg + 800 mg starch press 1 ton
IBU-sigma: 25 mg + 800 mg starch press

A     B

MESOPOROUS MATERIAL EXCIPIENTS FOR POORLY AQUEOUS SOLUBLE INGREDIENTS

CROSS-REFERENCE TO RELATED APPLICATIONS

The present application is a National Stage application under 35 U.S.C. §371 of PCT Application No. SG2009/000053, filed Feb. 18, 2009, which application claims priority to U.S. Provisional Patent Application No. 61/109,016, filed Oct. 28, 2008, the teachings of which are hereby incorporated by reference in their entirety for all purposes.

FIELD OF THE INVENTION

The technical field of this invention relates to solid dispersions or solutions involving mesoporous materials and poorly aqueous-soluble organic ingredients for pharmaceutical and specialty chemical applications. The formulation is prepared using a co-spray drying process.

BACKGROUND OF THE INVENTION

The poor solubility of active pharmaceutical ingredients (APIs) in water is one of the most challenging issues in the development of many pharmaceutical products for commercialization. More than one third of the drugs listed in the US Pharmacopoeia and half of the new chemical entities (NCEs), or new active ingredients are poorly water soluble or insoluble. The poorly water-soluble substances have a solubility of less than 10 g/L, in particular less than 5 g/L and more particularly, less than 1 g/l. Substances with aqueous solubility less than 0.1 g/L are classified as practically insoluble or an insoluble substance. When these drugs are administered, they usually have a very low bio-availability because of their poor solubility in the digestive fluid, causing erratic and incomplete absorption that may lead to a loss in therapeutic effect. Many NCEs fail to be commercialized due to their insolubility or poor solubility in water.

Much effort has been made to enhance the dissolution rate of poorly water-soluble drugs to increase bioavailability. One strategy is to improve dissolution rates through specific formulation methods, the most common being particle size reduction (see, Jinno, J. et al., *Journal of Controlled Release*, 111:56-64 (2006); Kirsten, Westesen et al., *Particles with modified physicochemical properties, their preparation and uses*, U.S. Pat. No. 6,197,349 (2001)), inclusion in cyclodextrins (see, Palmieri, G. F. et al., *ISTP Pharma Science* 7:174-181 (1997); Xiang, Tian-Xiang et al., *Pharmaceutical formulation for poorly water soluble camptothecin analogues*, U.S. Pat. No. 6,653,319 (2003)), the use of inert water-soluble drug carriers in solid solutions or dispersions, nanocrystalline (see, Wunderlich, et al., *Gelatin or collagen hydrolysate containing drug formulation that provides for immediate release of nanoparticle drug compounds*, U.S. Pat. No. 5,932,245 (1999)) or amorphous forms of APIs.

Among the various approaches, solid dispersion or solution formulations have been used to improve the dissolution rate of such kinds of drugs. Solid dispersions are usually formulated with soluble organic polymers (see, Yamane, Shogo et al., *Solid formulation with improved solubility and stability, and method for producing said formulation*, US Patent Pub. No. 2006/0153913 A1; Hoshino, Takafumi et al., *Solid dispersion preparation*, US Patent Pub. No. 2007/0248681A1), which typically have small-pore volume and low specific surface areas. Two reported methods involve the formation of solid drug dispersions in water-soluble carriers or the incorporation of surfactants and wetting agents (see, Storey, D. E. *Drug information Journal* 30:1039-1044 (1996)). Using water-soluble carriers, the solid dispersions are usually achieved through the processes of co-melting, quick cooling and pulverizing (see, Henricus, R. M. *Oral Solid solution formulation of poorly water-soluble active substance*, US Patent Pub. No. 2005/0008697 A1). It involves the melting of APIs together with other solid materials, such as PEG and glycol drug carriers, to form semi-solid and waxy in nature, and then hardened by cooling to very low temperatures. The mixture is then pulverized, sieved, mixed with relatively large amounts of excipients, and encapsulated into hard gelatin capsules or compressed into tablets. These operations are difficult to scale-up for the manufacture of dosage forms. Alternatively, the process of solvent removal (see, Straub, Julie et al., *Porous Drug matrices and Methods of manufacture thereof*, US Patent Pub. No. 2005/0048116 A1, Straub, Julie et al., *Porous Drug Matrices and Methods of manufacture thereof*, U.S. Pat. No. 6,932,983 B1 (2005)) can also be used to produce solid dispersions of drugs. The incorporation of soap-like surfactants in the formulation of poorly aqueous soluble drugs, may cause irritation side effects after oral administration in some cases.

Generally, the commercial application of solid dispersion has been very limited, primarily because of manufacturing difficulties and stability problems. These dosage forms developed often have drawbacks, such as poor product thermodynamic stability, issues with manufacturability such as poor batch-to-batch reproducibility and limitations in scaling-up for commercial production (see, Serajuddin, A. T. M. *Journal of Pharmaceutical Sciences*, 88:1058-1066 (1999)).

As mentioned above, another method is to reduce particle size, which is intended to increase the contact surface areas between the drug particle and the dissolution medium. The drawback of this technique lies in instability of particle size and agglomeration during post-milling storage, which causes variation in dissolution rate (see, Ng, W. K. et al., *Pharmaceutical Research* 25:1175-1185 (2008)). In some cases, a wide distribution of the particle size could have adverse side effects of gastric bleeding and nausea.

An alternative approach is to produce drugs in the amorphous form by co-grinding the drugs with other additives such as porous powder (see, Yonemochi, E. et al., *J. Colloid Interphase Sci.* 173:186-191 (1995)). Spray drying and quench are also applied to produce amorphous pharmaceutical products as the quick drying and cooling prevents the crystal growth (see, Gupta, P. et al., *Pharmaceutical Development and Technology*, 10:273-281 (2005)). However, the biggest challenge is to stabilize APIs to achieve an acceptable shelf-life because amorphous materials are generally thermodynamically unstable and tend to revert back to the crystalline form upon storage. The improved dissolution rates due to amorphization would be lost during transportation and storage when the amorphous APIs revert back to the crystalline form.

The discovery of a series of new ordered mesoporous material called MS41 family, having a regular pore size distribution that can be systematically varied between 2 and 10 nm, has opened up new possibilities in the field of catalysis, adsorption and pharmaceutical applications. Moreover, among the various structures of mesoporous silica materials, SBA-15 synthesized by nonionic polymer surfactant is the most extensively investigated due to its mesostructural diversity as well as the larger pore and thicker wall. The pore size is adjustable up to 30 nm. The feasibility to obtain different pore size and geometries offers wide potential for hosting molecules larger than the ones exhibited for classic microporous materials. In addition, the large surface areas of pore walls are occupied with high concentrations of silanol groups, which make the porous materials modifiable with different surface functional groups. Thus, the absorption properties are adjustable for different purposes of molecule hosting.

In view of the foregoing, there is a need for formulating drugs and specialty chemicals that are poorly water soluble, practically insoluble or insoluble. Formulations are needed which improve the dissolution rates of these compounds in order to improve their absorption in the digestive tract and thereby improve their efficacy. It is highly desirable to develop new formulations and methods that can amorphize an API to improve dissolution rates as well as stabilize the amorphous form during subsequent extended storage. The present invention satisfies these and other needs.

BRIEF SUMMARY OF THE INVENTION

The present invention provides pharmaceutical and specialty chemical formulations that utilize mesoporous materials or compositions, which possess high surface areas and large pore volumes as excipients. In certain aspects, the formulations are prepared by methods of using a co-spray drying process to prepare amorphous active ingredients, which are entrapped in the nanosized mesoporous channels with high homogeneity.

As such, in one embodiment, the present invention provides a pharmaceutical composition, comprising:
  a substantially water-insoluble pharmaceutical active ingredient; and
  a mesoporous composition having a plurality of nanopores, wherein the substantially water-insoluble pharmaceutical active ingredient is sprayed-dried together with the mesoporous composition to entrap the pharmaceutical active ingredient within the nanopores.

In certain aspects, an amorphous form of the active ingredient is kept very stable by confinement in the nanospace. The preparation process is both reproducible and can be easily scaled. In certain aspects, the present invention overcomes product instability concerns and manufacturability issues of current solid dispersion methods.

The present invention provides novel formulations and methods to improve the dissolution rates of poorly water-soluble active compounds, in particular active pharmaceutical ingredients (APIs). In certain aspects, a straightforward method of co-spray drying an active ingredient with a mesoporous material or composition is reproducible and can be easily scaled for commercial production as compared to other solid dispersion technologies.

As such, in another embodiment, the present invention provides a method for preparing a pharmaceutical composition, the method comprising:
  admixing a substantially water-insoluble pharmaceutical active ingredient with a mesoporous composition having a plurality of nanopores in a suitable solvent or mixture of solvents; and
  spray-drying the substantially water-insoluble pharmaceutical active ingredient with the mesoporous composition to entrap the pharmaceutical active ingredient within said nanopores, thereby producing said pharmaceutical composition.

In certain instances, the substantially water-insoluble pharmaceutical active ingredient is a member selected from an analgesic, an antipyretic, an anti-cholesterol or cholesterol-reducing agent, an anti-inflammatory agent, an antimicrobial, a decongestant and an antihistamine.

These and other aspects, objects and embodiments will become more apparent when read with the figures and detailed description which follows.

DETAILED DESCRIPTION OF THE INVENTION

I. Definitions

Figure 1:
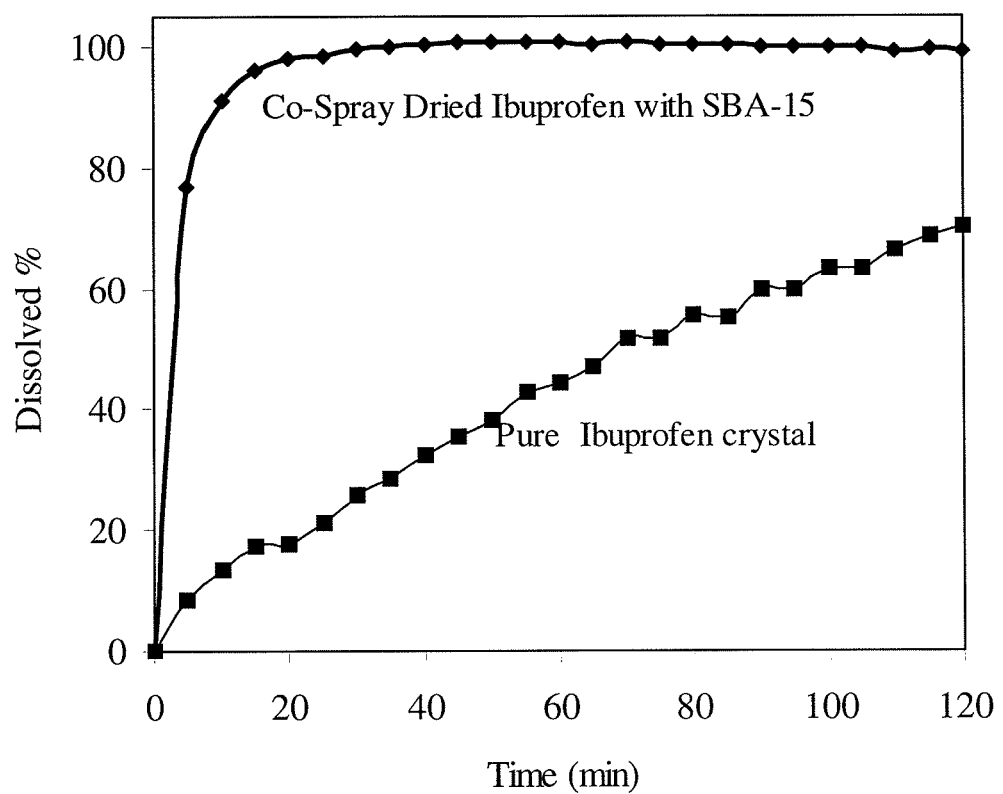
FIG. 1 illustrates dissolution profiles of spray-dried ibuprofen with SBA-15 (50:50 wt. %) and compared with pure ibuprofen crystal powder.

A "mesoporous composition" as used herein includes a porous solid having pores of a mean diameter of at least about 2 nm to about 50 nm. "Mean diameter" as used herein includes the mean of substantially all the pore diameters in the composition.

The terms "substantially water-insoluble," "poorly water-soluble" and "insoluble" include active ingredients which are insoluble, practically insoluble or only slightly soluble in water as those terms were defined in the U.S.P., Remington: "Pharmaceutical Science," 18th edition published by Mack Publishing Company and as used in the industry. In certain aspects, a poorly water-soluble compound or substantially water insoluble compound is preferably one having a solubility of ≤10 g/L, in particular ≤5 g/L and particularly preferably ≤1 g/L of water (at 25° C.).

The phrase "having improved water solubility" includes embodiments wherein a substantially water-insoluble drug as mentioned above can be used as a pharmaceutical product by a usual formulation method by improvement of its solubility in water. Specifically, it refers to the state that the solubility in water at about 20° C. is improved to about 5 times, preferably about 10 times, and more preferably 100 times or more using the methods described herein.

The term "amorphous" includes compounds having no particular kind, character, pattern or structure i.e., an indeterminate structure which is not crystalline. Due to the stable amorphous form, using the amorphous state of the active ingredient will significantly enhance the dissolution rate of the active ingredient over its crystalline form.

II. Embodiments

In one embodiment, the present invention provides a pharmaceutical composition, comprising:
 a substantially water-insoluble pharmaceutical active ingredient; and
 a mesoporous composition having a plurality of nanopores, wherein the substantially water-insoluble pharmaceutical active ingredient is sprayed-dried together with the mesoporous composition to entrap the pharmaceutical active ingredient within the nanopores.

A wide variety of active ingredients are suitable for use in the present invention. Suitable active ingredients include, without limitation, antacids, analgesics, anti-inflammatories, antipyretics antibiotics, antimicrobials, laxatives, anorexics, antihistamines, antiasthmatics, antidiuretics, anti-flatuents, antimigraine agents, biologicals (proteins, peptides, oligonucleotides, etc.) anti-spasmodics, sedatives, antihyperactives, antihypertensives, anti-cholesterols or cholesterol-reducing, tranquilizers, decongestants, beta blockers and combinations thereof. Fenofibrate and atorvastatin are particularly preferred in accordance with the present invention.

Substantially water-insoluble pharmaceutically active ingredients include, for example, cardiovascular drugs, e.g., cardiac glycosides, clofibrate and probucol; hypoglycemic drugs; sedatives/hypnotics, e.g., barbiturates; and antiepileptics, e.g., carbamazepine, mephenyloin and phenyloin; psychopharmacologic agents e.g., perphenazine, analgesic antipyretic and anti-inflammatory agents, e.g., naproxen, oxycodone and indomethacin; anti-neoplastic drugs such as almitrine; and antimicrobials such as erythromycin estolate. In accordance with the present invention, particularly preferred classes of insoluble drugs include: analgesics, antipyretics, anti-inflammatory agent, antimicrobials, decongestants and antihistamines. Ibuprofen is particularly preferred in accordance with the present invention.

Other drugs or bioactive agents suitable for the present invention include anesthetics such as butanilicain, fomocain, lidocain, prilocaln, tetracain and etomidate; antibiotics such as fosfomycin, fosmidomycin and rifapentin; antihypertensives such as minoxidil, dihydroergotoxine and endralazine; antihypotensives such as dihydroergotamine; systemic antimycotics such as ketoconazole, miconazole and griseofulvin; antiphiogistics such as indomethacin, diclofenac, ibuprofen, ketoprofen and pirprofen; antiviral agents such as aciclovir, vidarabin and immunoglobulines; ACE inhibitors such as captopril and enalapril; betablockers such as propranolol, atenolol, metoprolol, pindolol, oxprenolol and labetalol; bronchodilators such as ipratropiumbromide and sobrerol; calcium antagonists such as diltiazem, flunarizin, verapamil, nifedipin, nimodipin and nitrendipin; cardiac glycosides such as digitoxin, digoxin, methyldigoxin and acetyldigoxin; cephalosporins such as ceftizoxim, cefalexin, cefalotin and cefotaxim; cytostatics such as chlormethin, cyclophosphamid, chlorambucil, cytarabin, vincristin, mitomycin C, doxorubicin, bleomycin, cisplatin, taxol, penclomedine and estramustin; hypnotics such as flurazepam, nitrazepam and lorazepam; psychotropic drugs such as oxazepam, diazepam and bromazepam; steroid hormones such as cortisone, hydrocortisone, prednisone, prednisolone, dexamethasone, progesterone, pregnanolone, testosterone and testosterone undecanoate; vasodilators such as molsidomin, hydralazin and dihydralazin; cerebral vasodilators such as dihydroergotoxin, ciclonicat and vincamin; ubiquinones and their analogues such as ubidecarenone and atovaquon; lipophilic vitamins such as vitamin A, E, D, K and their derivates; insecticides, herbicides and pesticides such as acephate, cyfluthrin, azinphosphomethyl, cypermethrin, fenclofos, permelthrin, piperonal, tetramethrin and trifluralin.

In certain aspects, the substantially water-insoluble pharmaceutical active ingredient is present in the composition at about 0.1% to about 75% w/w, preferably, at about 10% to about 60% w/w and more preferably, at about 30% to about 50% w/w.

The active ingredients of the present invention are preferably pharmaceutical active ingredients. However, the active ingredients include agrochemical and specialty chemicals as well.

A. Mesoporous Materials

In certain preferred aspects, the pharmaceutical composition of the present invention utilizing a mesoporous composition is selected from the group consisting of silica, carbon, alumina, carbides, silicides, nitrides and oxides. In certain aspects, the mesoporous composition comprises an oxide, such as a silicate. In certain preferred aspects, the mesoporous composition is selected from the group of MCM-41, MCM-48, SBA-15, MCF, MSU and CMK-3, with SBA-15 and MCM-41 being especially preferred (see, Vallet-Regí et al., *Angewandte Chemie* International Edition, 46: 7548-7558 (2007)).

In one aspect, the mesoporous material is within the MS41 family, having regular pore size distribution that can be systematically varied between 2 nm and 10 nm (see, Ciesla et al. *Microporous Mesoporous Mater.* 27: 131-149 (1999)). In certain aspects, SBA-15 can be synthesized by a nonionic polymer surfactant and has mesostructural diversity as well as large pores and thick walls. The pore size is adjustable up to 30 nm. The large surface areas of pore walls are occupied with high concentrations of silanol groups, which make the porous materials modifiable with different surface functional groups. Thus, the absorption properties are adjustable for different purposes of molecule hosting. In certain aspects, the mesoporous materials have surface areas of about 300 to about 2000 $m^2/g$ and more preferably have specific surface areas of about 400 to 1200 $m^2/g$.

In certain preferred aspects, the use of mesoporous compositions enable the use of the amorphous state of one or more active ingredient(s). The amorphous form of the active ingredient is stabilized in the nanosized mesoporous structures even under stress storage conditions.

In certain aspects, the mesoporous composition has a particle size of about 0.1 μm to about 100 μm, preferably the mesoporous composition has a particle size of about 0.3 μm to about 50 μm and more preferably, the mesoporous composition has a particle size of about 0.5 μm to about 30 μm. For the particles with rod-like morphology, the diameter of the particles is about 0.1 μm to about 50 μm and more preferably, the mesoporous composition has a mean diameter about 0.2 μm to about 30 μm.

In certain aspects, the mesoporous composition comprises a plurality of pores having a mean diameter of about 1 nm to about 100 nm, preferably having a mean diameter of about 1.5 nm to about 50 nm and more preferably having a mean diameter of about 2 nm to about 30 nm.

In certain other aspects, the mesoporous composition comprises a plurality of pores having a mean volume of about 0.2 $cm^3/g$ to about 4.0 $cm^3/g$ and more preferably, a mean volume of about 0.8 $cm^3/g$ to about 3.0 $cm^3/g$.

B. Modified Release

In certain aspects, the formulations of the present invention deliver a drug at a controlled rate (e.g. sustained, prolonged, extended or retarded release). It is often practical to design dosage forms that use a combination of the foregoing mechanisms to achieve a particularly desirable release profile for a particular active ingredient. It will be readily recognized by those skilled in the art that a dosage form construct that offers multiple nanopores, such as for example a plurality of pore sizes and volumes, is particularly advantageous for its flexibility in providing a number of different mechanisms for controlling the release of one or more active ingredients.

One objective of modified release dosage forms is to provide a desired blood concentration versus time (pharmacokinetic, or PK) profile for the drug. Fundamentally, the PK profile for a drug is governed by the rate of absorption of the drug into the blood, and the rate of elimination of the drug from the blood. To be absorbed into the blood (circulatory system), the drug must first be dissolved in the gastric fluids. For those relatively rapidly absorbed drugs whose dissolution in gastric fluids is the rate limiting step in drug absorption, controlling the rate of dissolution (i.e., drug release from the dosage form) allows for the control of the rate of drug absorption into the circulatory system of a patient. The type of PK profile, and correspondingly, the type of dissolution or release profile desired, depends on, among other factors, the particular active ingredient, the mesoporous composition and physiological condition being treated.

One particularly desirable PK profile is achieved by a dosage form that delivers a delayed release dissolution profile, in which the release of one or more doses of drug from the dosage form is delayed for a pre-determined time after contacting of the dosage form by a liquid medium, such as for example, after ingestion by the patient. The delay period ("lag time") can be followed either by prompt release of the active ingredient ("delayed burst"), or by sustained (prolonged, extended, or retarded) release of the active ingredient ("delayed then sustained"). These PK profiles can be engineered using various combination of mesoporous materials, active ingredients (whether amorphous or crystalline) and coatings.

In certain aspects, the present invention provides formulations wherein a portion of the API is amorphous and another portion of the API is crystalline. The APIs may be the same or different. In this manner, the amorphous API has a rapid release, whereas the crystalline form is released-slowly, or is a controlled-release. For example, an amorphous drug can be loaded in the pore volume, whereas the crystalline particles can be outside the mesoporous matrix. In certain embodiments, the amorphous portion is one drug, whereas the crystalline drug is another drug. In certain instances, the solid dispersion described herein exists exclusively in an amorphous form.

In certain other aspects, the active ingredient of the formulation according to the invention is contained in a mesoporous matrix as the crystalline form for delayed release. The architecture and volume of the pores can be modified in order to achieve a tailored release profile.

The active agent, either in a crystalline form, an amorphous form, or a combination thereof, may be modified to form delayed release granules. In certain aspects, the granules are coated with a coating layer of a dissolution-retarding coating. In their uncoated form, such granules are rapid release granules, which release their content more rapidly than coated granules. The dissolution-retarding coating may be a polymeric material, for example an enteric polymer (the term "enteric polymer" is a term of the art referring to a polymer which is preferentially soluble in the less acid environment of the intestine relative to the more acid environment of the stomach).

Examples of enteric polymers include cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, and the like. These can be used either alone or in combination. The enteric coating may also include starch and/or dextrin.

Preferred enteric coating materials are the commercially available "Eudragit" enteric polymers, such as "Eudragit L®", "Eudragit S®" and "Eudragit NE®" used either alone or with a plasticizer. Such coatings are normally applied using a liquid medium, and the nature of the plasticizer, depends upon whether the medium is aqueous or non-aqueous. Aqueous plasticizers include propylene glycol or "Citroflex®" or Citroflex A2®" (mainly triethyl citrate or acetyl triethyl citrate). Nonaqueous plasticizers include these, and also diethyl and dibutyl phthalate and dibutyl sebacate.

In certain other aspects, the pharmaceutical compositions of the present inventions have an increased dissolution profile compared to a pharmaceutical composition without a mesoporous composition or material.

In other instances, the compositions and methods herein use silanol groups of the mesoporous materials to functionalize the surfaces to make grafted organic silanes ((RO)$_3$SiR'). In this manner, the active pharmaceutical ingredient has increased interaction with the surface. In certain other instances, the surface is functionalized with amino groups. This too can modify drug release (see, Vallet-Regi et al., *Angewandte Chemie* International Edition, 46: 7548-7558 (2007)).

C. Method of Making

The present invention provides methods for making or preparing the formulation described herein. In certain aspects, the methods relate to preparing solid dispersions, having the ability to form the amorphous state of one or more active ingredient(s) inside the solid dispersions. The amorphous form of an active ingredient is stabilized in the nanosized mesoporous structures even under stress of storage conditions.

In certain aspects, the formulation is prepared by a process of co-spray drying of mesoporous materials with a poorly aqueous soluble active ingredient dissolved in suitable solvent or mixture of solvents. The final solid dispersion comprises on a weight basis (percent by weight): (a) 1% to 75% of active ingredient (b) and the balance being porous inorganic materials such as mesoporous silica and carbon, up to 100 weight percent. In certain aspects, the active ingredient can be ibuprofen, fenofibrate, indomethacin, carbamazapine and ursodeoxycholic acid.

In one embodiment, the present invention provides, a method for preparing a pharmaceutical composition, comprising:

admixing a substantially water-insoluble pharmaceutical active ingredient with a mesoporous composition having a plurality of nanopores in a suitable solvent or mixture of solvents; and spray-drying the substantially water-insoluble pharmaceutical active ingredient with the mesoporous composition to entrap the pharmaceutical active ingredient within said nanopores, thereby producing the pharmaceutical composition.

In one aspect, the spray drying is implemented by dissolving a poorly water-soluble drug in an organic solvent such as ethanol. Suitable solvents or co-solvents include $C_1$-$C_6$ alkanols, ketones, esters, ethers, aliphatic hydrocarbons, aromatic hydrocarbons, halogenated solvents, cycloaliphatic solvents, aromatic heterocyclic solvents, and mixtures thereof. Next, a mesoporous powder is then dispersed into the solution under stirring conditions for sufficient time to make a solid suspension (e.g., overnight). The solid dispersion can then be co-spray dried.

In general, a typical spray-drying apparatus comprises a drying chamber, atomizing means for atomizing a solvent-containing feed into the drying chamber, a source of heated drying gas that flows into the drying chamber to remove solvent from the atomized solvent-containing feed and product collection means located downstream of the drying chamber. Examples of such apparatus include a Buchi mini spray dryer B290. In certain instances, the spray-drying apparatus is equipped with a two-fluid nozzle for atomizing the solvent-containing feed. Such nozzles produce small droplets of feed solution, typically 5 to 30 μm in diameter, and turbulent mixing of the liquid feed droplets and drying gas, leading to rapid drying of the fluid to form solid particles. Such spray-drying apparatus are effective in forming substantially amorphous and substantially homogeneous solid-amorphous dispersions of drug and mesoporous compositions or materials. Inlet and outlet temperature can be at 25° C.~150° C. (e.g., 81° C.) and 25° C.~120° C. (e.g., 50-55° C.), respectively.

Although spray-drying is a preferred method for preparation, the methods herein are not so limited. In addition to techniques of spray drying, ball milling, impregnation, co-quench and mixing processes can be employed to load poorly soluble drugs into mesoporous materials. Other methods include for example, a dry blending (i.e., direct compression), or a wet granulation process as known in the art. In a dry blending (direct compression) method, the active ingredient or ingredients, together with the excipients, are blended in a suitable blender, than transferred directly to a compression machine for pressing into tablets. In a wet granulation method, the active ingredient or ingredients, appropriate excipients, and a solution or dispersion of a wet binder (e.g., an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g., planetary mixers; high shear mixers; and fluid beds, including rotary fluid beds. The resulting granulated material is dried, and optionally dry-blended with further ingredients, e.g., adjuvants and/or excipients such as for example lubricants, colorants, and the like. The final dry blend is then suitable for compression. Methods for direct compression and wet granulation processes are known in the art.

The porous inorganic materials are typically in the size range of 0.1 μm to 100 μm with pore size ranging from 1 to 100 nm and pore volume ranging from 0.2 to 4.0 cm$^3$/g.

Advantageously, the methods are effective to improve the dissolution profiles of poorly aqueous soluble pharmaceutical active ingredients. The solid dispersions prepared possess distinct physical stability against re-crystallization under stress test conditions at 40° C./75% RH for 1 year. Without being bound by any particular theory, it is believed that this significant improvement is achieved by the entrapment of amorphous drugs within the nanosized pores of mesoporous materials by co-spray drying. The amount of drug incorporated in the mesoporous matrix can attain a proportion of up to 75% w/w in final solid powder, depending on the amount of drug added during preparation.

In certain embodiments, when the active ingredient is co-spray-dried with, for example, mesoporous SBA-15 submicron, most of the active ingredient is confined inside the porous structure of SBA-15, thus the outer surface morphology is not obviously changed. The internal pore channel is filled with the active ingredient and the outer surface can then be coated with a very thin layer of active ingredient (<10 nm). The solid pore wall prevents the re-crystallization of the confined active ingredient during the storage at 40° C./75% RH. In addition, the amount of surface loaded active ingredient can be controlled.

Mesoporous materials, including silica, carbon, and alumina are used as a matrix to formulate poorly soluble drugs with the objective of nanoconfinement of poorly water-soluble drugs and stabilize the amorphous form with long shelf-life.

The storage stability was tested in severe storage condition of 75% relative humidity and temperature of 40° C., denoted as 40° C./75% RH.

D. Additional Excipients

In certain embodiments, additional excipients are used in the formulations of the present invention. For example, suitable fillers include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble materials such as microcrystalline cellulose or other cellulosic derivatives, water-insoluble materials such as dicalcium phosphate, tricalcium phosphate and the like and mixtures thereof.

Suitable binders include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants include sodium starch glycolate, cross-linked polyvinylpyrrolidone, cross-linked carboxymethylcellulose, starches, microcrystalline cellulose, and the like.

Suitable lubricants include long chain fatty acids and their salts, such as magnesium stearate and stearic acid, talc, glycerides and waxes.

Suitable glidants for making a core or core portion by compression, include colloidal silicon dioxide, and the like.

Suitable swellable erodible hydrophilic materials for use as release-modifying excipients include: water swellable cellulose derivatives, polyalkalene glycols, thermoplastic polyalkalene oxides, acrylic polymers, hydrocolloids, clays, gelling starches, and swelling cross-linked polymers, and derivatives, copolymers, and combinations thereof. Examples of suitable water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkalene glyclols include polyethylene glycol. Examples of suitable thermoplastic polyalkalene oxides include poly (ethylene oxide). Examples of suitable acrylic polymers include potassium methacrylate-divinylbenzene copolymer, polymethylmethacrylate, CARBOPOL (high-molecular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellulose sodium.

Suitable insoluble edible materials for use as release-modifying excipients include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

In certain instances, the formulations of the present invention can be coated by known methods in order to provide taste-masking, odor-masking, to make the preparation enteric, or to achieve sustained release of the preparation. Examples of the coating agent can include enteric polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate and carboxymethylethylcellulose; polymers soluble in stomach such as polyvinyl acetal diethylaminoacetate and aminoalkyl methacrylate copolymer; and the water-soluble polymers.

The pharmaceutical formulations according to the invention may in addition contain as further constituents conventional pharmaceutical auxiliary substances such as fillers, for example lactose, microcrystalline cellulose (MCC) or calcium hydrogen phosphate, as well as glidants, intestinal lubricants and flow regulating agents, for example talcum, magnesium stearate, stearic acid and/or highly dispersed silicon dioxide, whose total weight in the tablet is between 0 and 80 wt %, preferably between 5 and 65 wt %.

In certain embodiments, the pharmaceutical formulations can be a self-contained unitary object, such as a tablet or capsule. Typically, the formulation is compressed or molded in a tablet, hard or soft capsule, suppository, or a confectionery form such as a lozenge, nougat, caramel, fondant, or fat based composition.

III. EXAMPLES

Example 1

1.0 g of Ibuprofen and 1.0 g of submicron mesoporous silica materials were dispersed in 100 mL ethanol under stirring overnight. The suspension was spray-dried in a Buchi Spray Drier B290. The inlet temperature was set to 81° C. and the outlet temperature was ~50° C. The pump speed was set to "20". Dissolution condition: 50 mg spray-dried ibuprofen with SBA-15 and 25 mg of pure ibuprofen (Sigma) crystal were used for dissolution testing in 900 mL 0.1N HCl at 37° C. Stirring speed is 100 rpm. Sample was taken by auto sampling system at interval of 5 min. UV reading was taken at wavelength 222 nm.

As indicated in FIG. 1, the dissolution rate of spray-dried ibuprofen is significantly enhanced, as compared with a commercial ibuprofen in crystalline form (Sigma). In 15 min, 95.6% of spray-dried ibuprofen with SBA-15 is dissolved, whereas only 17.5% of pure ibuprofen crystal is dissolved. The dissolution profile was measured using VK7010 (Varian Co) USP dissolution tester with flow cell online UV-vis analysis system. Stirring rate is 100 rpm and vessel temperature is set at 37° C.

Figure 2:
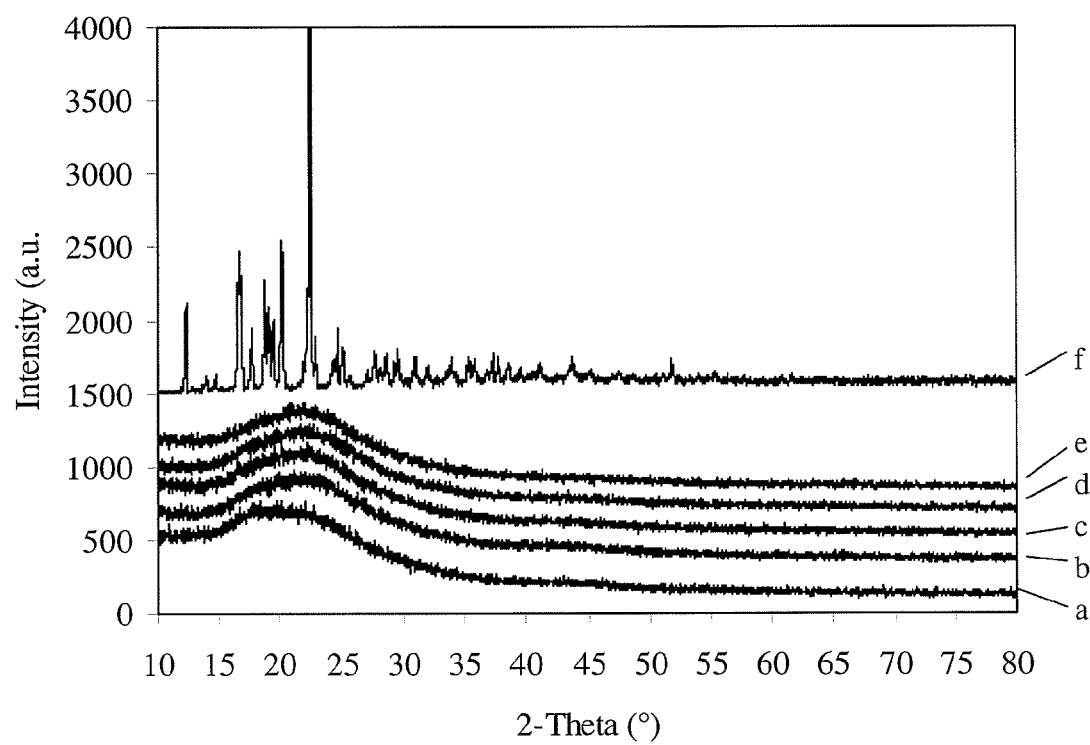
FIG. 2 illustrates XRD patterns of co-spray-dried ibuprofen with mesoporous SBA-15 after storage at 40° C./75% RH for (a) fresh (b) 3 months, (c) 6 months, (d) 10 months, (e) 12 months; and (f) a control sample of commercial ibuprofen crystal.

The improved dissolution rate of SBA-15 formulated ibuprofen via spray-drying is attributed to the amorphous state of ingredient formed in the pores of SBA-15. Moreover, the amorphous form of ibuprofen within mesoporous materials is physically stable against re-crystallization under the testing condition of 40° C./75% relative humidity (RH). As shown in FIG. 2, the freshly spray-dried ibuprofen with SBA-15 exhibited typical amorphous characteristics. A broad peak at 2-θ of 15-30° is typical in diffraction patterns of X-ray amorphous silica. No X-ray diffraction peak assigned to the crystalline form of ibuprofen was observed. The amorphous form shows superior stability under severe condition of 40° C./75% RH. No crystal growth could be detected by XRD after 3, 6, and 12 months.

Figure 3:
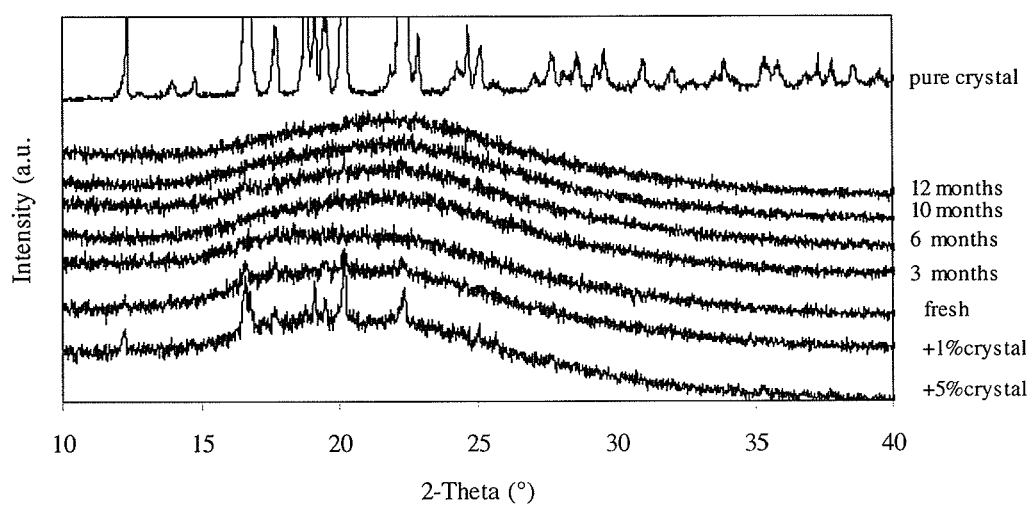
FIG. 3 illustrates XRD patterns of co-spray-dried ibuprofen/SBA-15 after storage and compared with samples having 1 wt. % and 5 wt. % of commercial ibuprofen crystal added.

Additionally, in FIG. 3, crystalline behavior resurfaces when some crystals of ibuprofen are added and mixed with the amorphous solid formulation containing the drug incorporated in SBA-15. This shows that the solid formulation is exclusively amorphous in nature and the degree of crystalline structure can be modified only by addition of ibuprofen crystals to the solid dispersion.

The enhanced stability of spray drying ibuprofen with SBA-15 under severe condition is attributed to the mesoporous structure of SBA-15 materials, which possesses nano-sized pore channels and high porosity. When ibuprofen is spray-dried with SBA-15 submicron particles, most of the ibuprofen is stored in the nano-pore channels. When SBA-15 submicron is spray-dried without ibuprofen, the pore volume is 1.019 $cm^3/g$; however it reduced to 0.0913 $cm^3/g$ when it is spray-dried with ibuprofen (50:50 wt). As the true density of ibuprofen is 1.076 $g/cm^3$, 89.9% of ibuprofen is loaded into the pore channels inside mesoporous particles. The amorphous pore wall prevents the confined ibuprofen to be crystallized.

Figure 4:
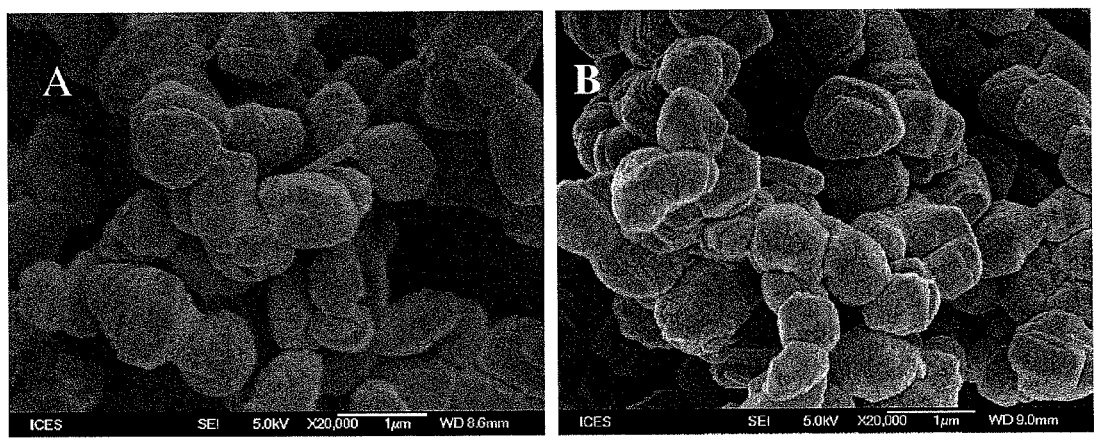
FIG. 4 illustrates a SEM image of (A) spray-dried SBA-15 submicron particles and (B) co-spray-dried ibuprofen with SBA-15 (50:50 wt).
Figure 5:
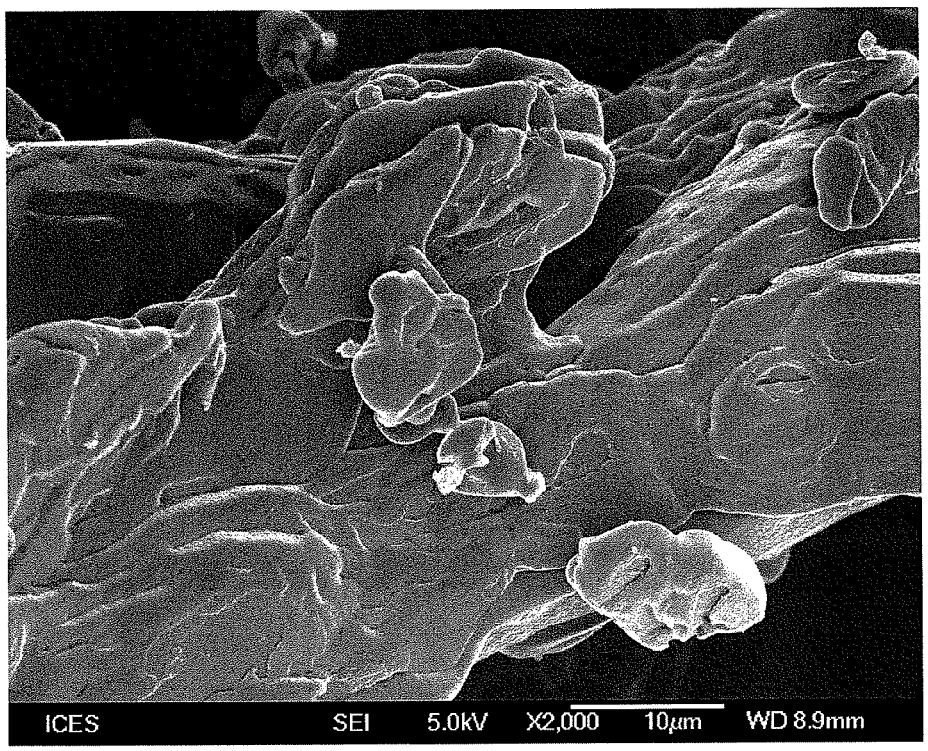
FIG. 5 illustrates a SEM image of spray-dried ibuprofen (Sigma).
Figure 6:
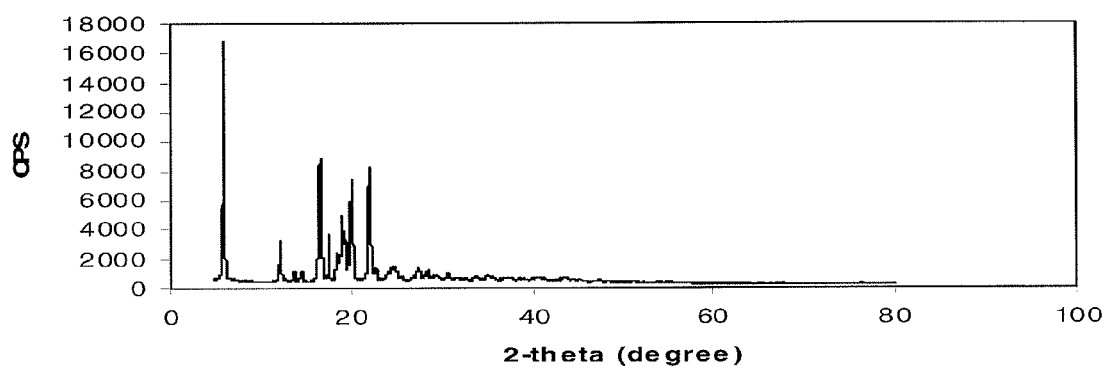
FIG. 6 illustrates a XRD pattern of spray-dried ibuprofen (Sigma).
Figure 7:
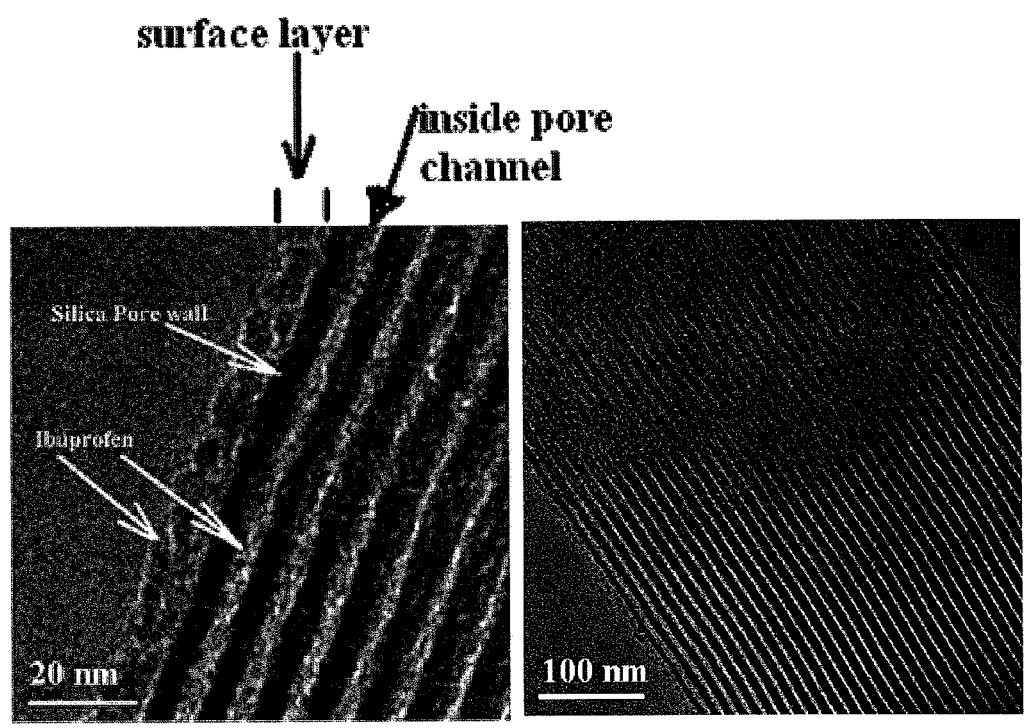
FIG. 7 illustrates a TEM image of ibuprofen co-spray-dried with SBA-15 submicron (left: high magnification, right: low magnification).

FIGS. 4A and B illustrate the SEM morphology of spray-dried SBA-15 submicron particles and spray-dried ibuprofen with SBA-15 submicron particles (50:50 wt). It can be seen that the morphology of submicron SBA-15 particles is not obviously changed after spray-dried with same weight ratio of ibuprofen. No large particles of ibuprofen are formed. When pure ibuprofen is spray-dried, particles larger than several tens micron meter is observed as shown in FIG. 5. The X-ray diffraction pattern as shown in FIG. 6 further confirms the crystalline behavior of spray-dried ibuprofen. FIG. 7 highlights the distribution of ibuprofen in the pore channels and on the outer surface of SBA-15 after spray drying.

Example 2

Figure 8:
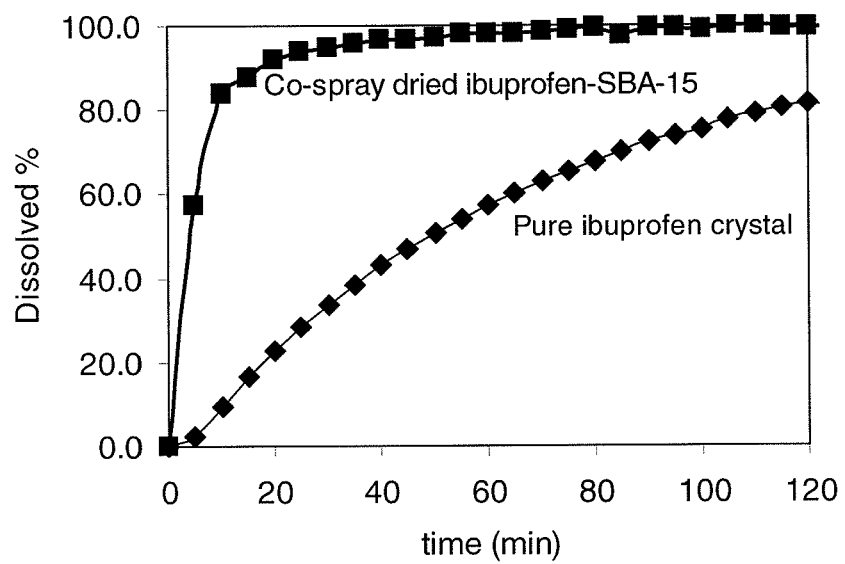
FIG. 8 illustrates tablet form dissolution profiles of co-spray-dried ibuprofen with SBA-15 (50:50 wt) and compared with commercial ibuprofen in the crystalline form.

Ibuprofen is co-spray-dried with SBA-15 submicron particles using the same procedures as Example 1. To evaluate the dissolution rates in the tablet form, 50 mg of ibuprofen spray-dried with SBA-15 (50:50 wt) is mixed with 0.8 g of cornstarch and pressed in a die with diameter of 13 mm at press of 1 ton. A control sample of 25-mg ibuprofen in the crystalline form (commercial) is tableted with cornstarch with the same procedure. The dissolution is performed using the same method as in Example 1. The tablet form dissolution profile as illustrated in FIG. 8 is similar to that observed in the powder form. 87.9% of the spray-dried ibuprofen in the tablet form dissolves within 15 min as compared to only 16.4% of ibuprofen dissolved in the crystalline form.

Example 3

Figure 9:
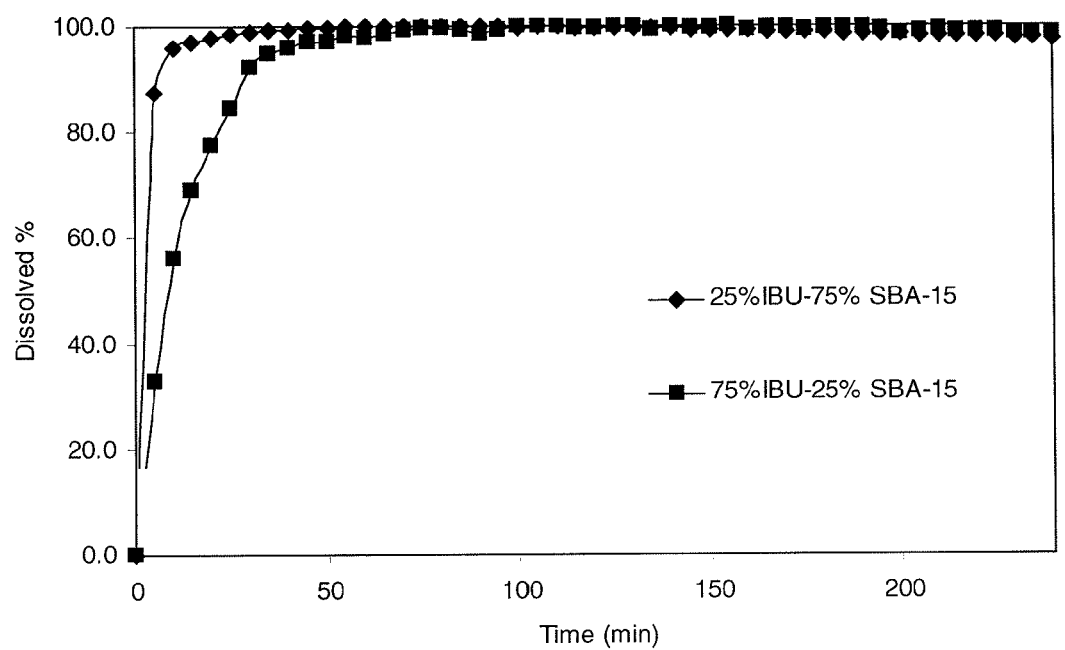
FIG. 9 illustrates dissolution profiles of spray-dried ibuprofen/SBA-15 with different drug loadings of 25% and 75%.
Figure 10:
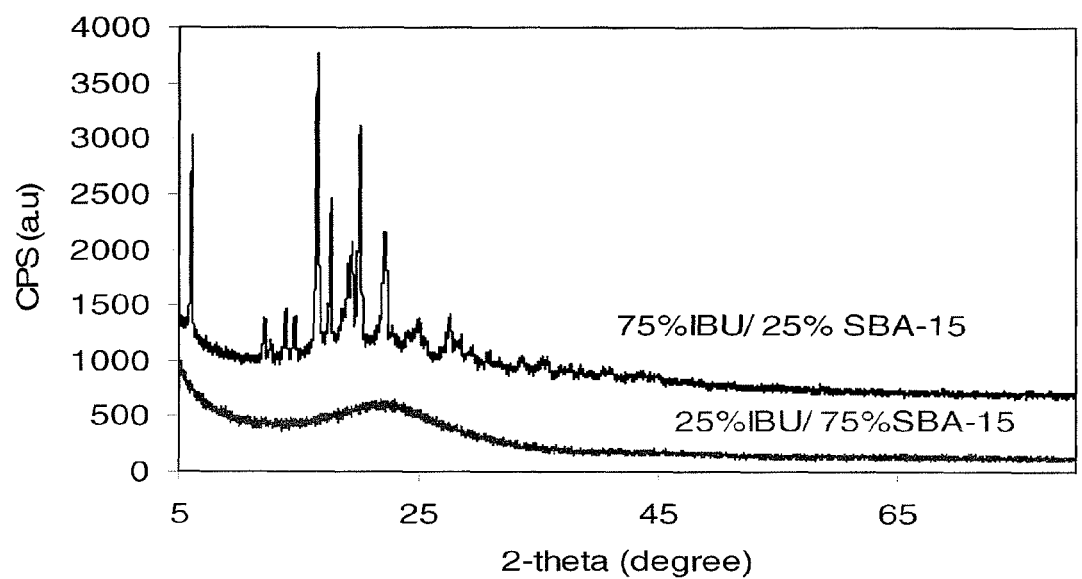
FIG. 10 illustrates a XRD pattern of spray-dried ibuprofen/SBA-15 with different drug loadings of 25% and 75%.

FIG. 9 illustrates the dissolution of the spray-dried ibuprofen at drug loading ratios of 25% and 75%. The sample exhibits very high dissolution rate when the formulation contains 25% of ibuprofen and 75% of SBA-15: 97.1% of active ingredient is dissolved in 15 min. When the formulation contains 75% of ibuprofen and 25% of SBA-15, the dissolution reaches 68.9% in 15 min, which is much higher than commercial pure ibuprofen in the crystalline form although it is slightly delayed as compared to the samples with lower drug loadings. The pore volume is not enough to host ibuprofen in solid dispersion with high drug loading of 75%, and the remaining ibuprofen forms crystalline particles outside the mesoporous matrix. The partially crystallized ibuprofen can be detected by XRD as shown in FIG. 10.

Example 4

Figure 11:
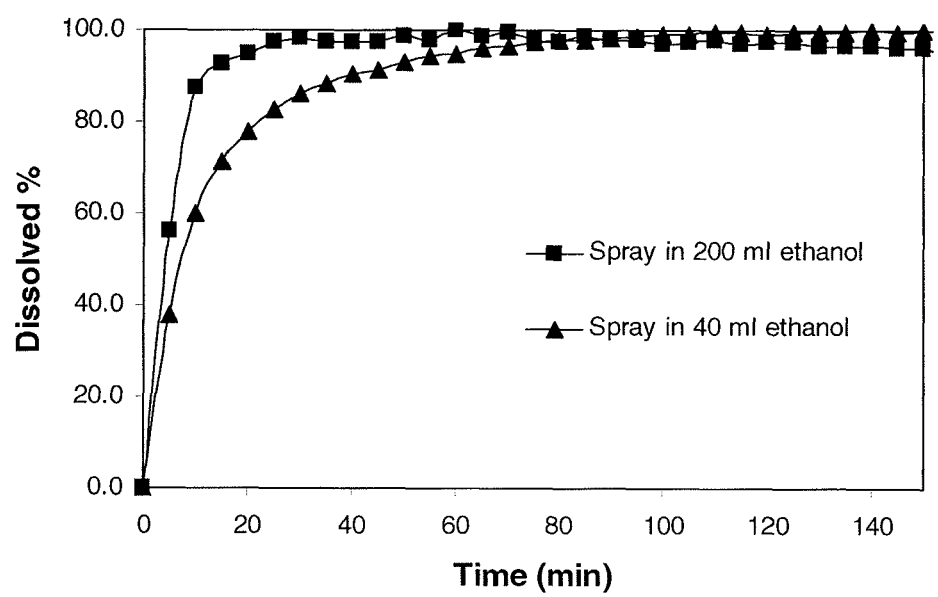
FIG. 11 illustrates a dissolution profile of ibuprofen/SBA-15 spray-dried in different amounts of ethanol.

1.0 g of Ibuprofen and 1.0 g of submicron mesoporous silica materials were dispersed in 40 mL and 200 mL of ethanol under stirring overnight. The suspension was spray-dried and 50 mg of this suspension (50:50 wt of ibuprofen: SBA-15) is mixed with 0.8 g of cornstarch and pressed in a die with diameter of 13 mm at press of 1 ton. The dissolution is performed using same method in Example 1. FIG. 11 illustrates the dissolution profile of the spray-dried ibuprofen dispersed in different amounts of ethanol. The dispersion in 200 mL of ethanol yielded a higher dissolution rate compared to the dispersion in 40 mL of ethanol.

Example 5

Figure 12:
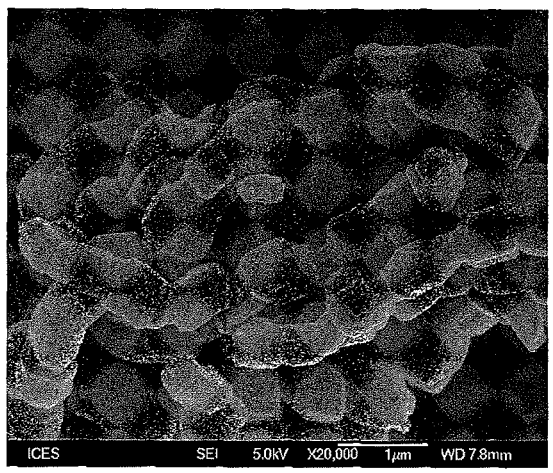
FIG. 12A-B illustrates SEM images of SBA-15 particles of different sizes (A: micron particles up to ten microns; B: nanoparticles with size of 200-400 nm).
Figure 12:
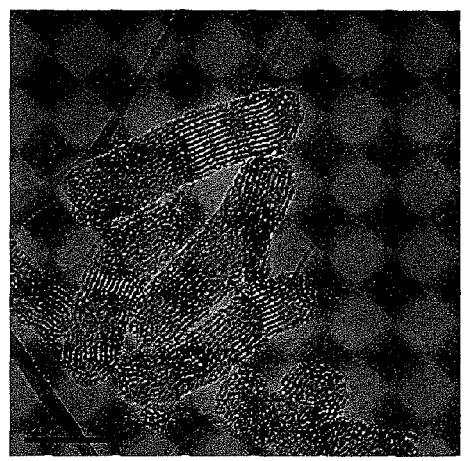
Figure 13:
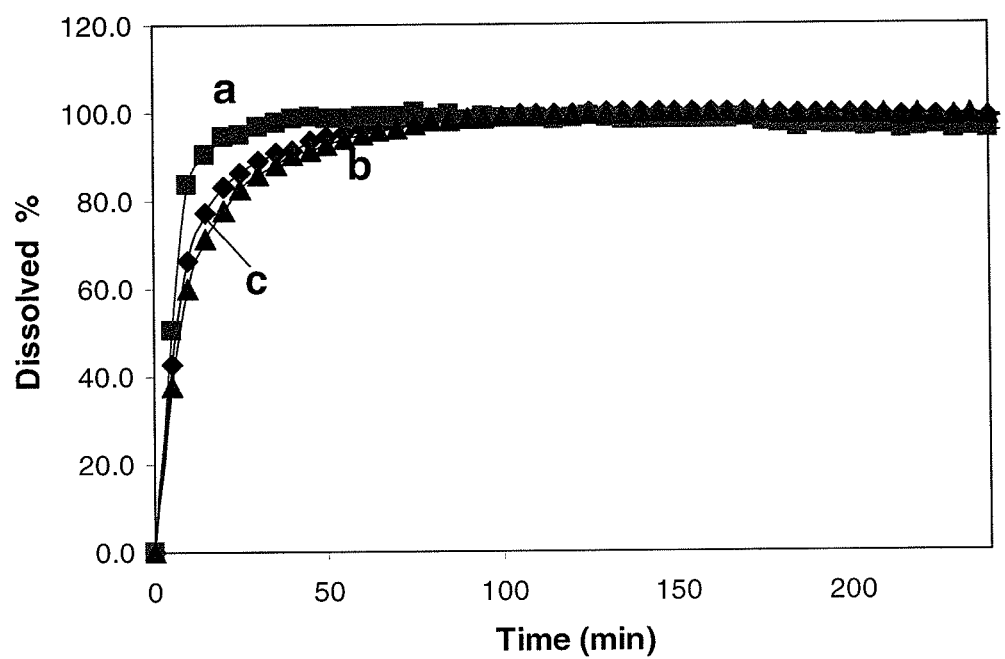
FIG. 13 depicts the dissolution profile of ibuprofen spray-dried with SBA-15 particles of different sizes.

The mesoporous silica based materials with different particle sizes are used to formulate poorly water-soluble ibuprofen by spray-drying. The mesoporous nanoparticles with size of 200-400 nm and large particles up to ten microns as shown in FIG. 12 are used. The pore size of these materials is almost the same as they are prepared using the same method. When ibuprofen is spray-dried with mesoporous materials with different particle size, it is found that the nanoparticle matrix exhibit a faster dissolution rate. When dissolution tests of the tablet forms are carried out, as illustrated in FIG. 13, the sample of ibuprofen spray-dried with mesoporous nanoparticles dissolve 90.5% in 15 min, whereas the ibuprofen sample spray-dried with large mesoporous particles dissolves 71% under conditions. The faster release of active ingredient from its pore channels is attributed to shorter length of pore channels.

Example 6

Poorly water-soluble model drug, ibuprofen, is formulated with SBA-15 submicron mesoporous particle by ball-milling, impregnation, co-quench and mixing.

Ball milling: 1.0 g of ibuprofen and 1.0 g of SBA-15 submicron particles was co-milled in a ball mill (Fritsch) at rotating rate of 200 rpm for 1 h.

Impregnation: 0.5 g of ibuprofen was dissolved in 5 mL of ethanol. 0.5 g of SBA-15 submicron particles was added to ibuprofen solution. Ethanol was evaporated at room temperature under stirring overnight. The obtained powder was dried in a vacuum at room temperature.

Co-quench: 1.0 g of ibuprofen was fully mixed with 1.0 g of SBA-15 submicron particles. The mixture was heated to above 120° C. to melt ibuprofen. The hot mixture was quenched by liquid nitrogen, and the solid was kept in a vacuum at room temperature.

Mixing: 1.0 g of ibuprofen and 1.0 g of SBA-15 submicron particles were ground in a mortar and pestle for 5 min.

Figure 14:
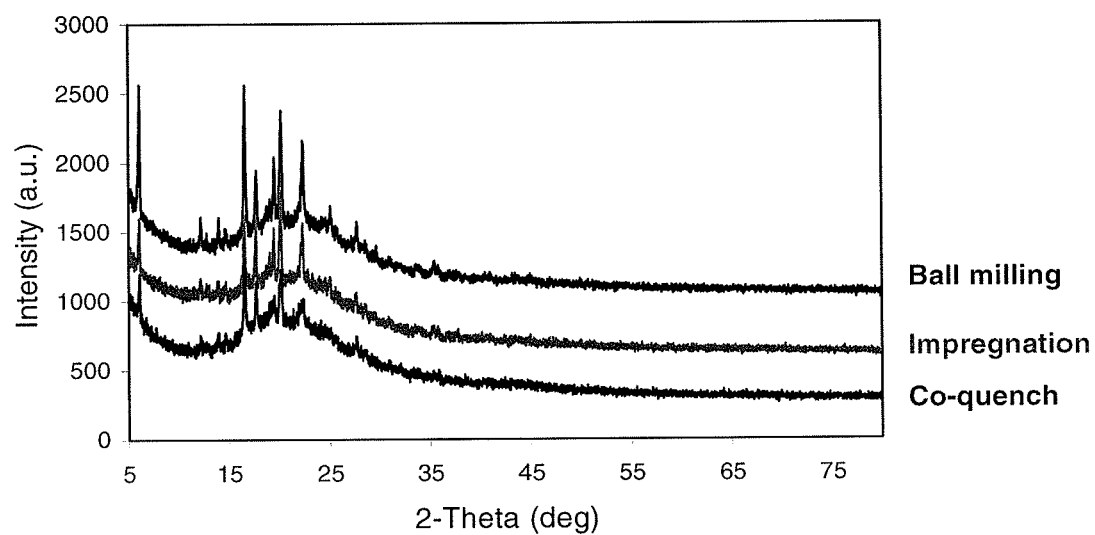
FIG. 14 illustrates a XRD pattern of formulated ibuprofen formulated with SBA-15 by ball milling, impregnation and co-quench.

The dissolution rates of ibuprofen formulated using the above methods are analyzed in powder form and the dissolution data in 15, 30, 45 and 60 min are listed in Table 1. Although ball milling, mixing, impregnation and co-quench methods exhibit higher dissolution rate than pure commercial ibuprofen, these methods are inferior to spray-drying. XRD investigation as shown in FIG. 14 indicates that only spray-drying with SBA-15 submicron particles results in a fully X-ray amorphous form, while all other methods give rise to partially crystallized form. Thus, among all formulation methods used, spray-drying is shown to be the best procedure to produce ibuprofen in an amorphous form, which exhibits the highest dissolution rates.

TABLE 1

Dissolution test data of ibuprofen formulated using different methods

| Formulation | 15 min | 30 min | 45 min | 60 min |
|---|---|---|---|---|
| Pure crystal (commercial) | 17.5% | 25.6% | 35.6% | 44.5% |
| Spray dry | 95.9% | 99.5% | 100% | 100% |
| Spray dry (Tablet with cornstarch) | 87.9% | 94.8% | 96.8% | 98.1% |
| Ball milling | 36.6% | 52.4% | 62.5% | 69.6% |
| Mixing | 31.9% | 51.7% | 64.6% | 73.5% |
| Impregnation | 49.1% | 57.3% | 62.9% | 66.4% |
| Co-quench | 33.0% | 48.7% | 59.1% | 67.2% |

(dissolution conditions: 25 mg ibuprofen or equivalent amount ibuprofen formulated with SBA-15 submicron particles; dissolution medium 900 mL 0.1N HCl at 37° C., stirring rate 100 rpm).

Example 7

Fenofibrate, an ester derived from fibric acid, is used to reduce the level of cholesterol and triglycerides (see, Palmieri, G. F. et al., *STP pharma Science* 6:188-194 (1996)). This drug has extremely poor aqueous solubility. Much effort has been reported to improve its solubility and dissolution rate, such as micronization using supercritical carbon dioxide (see, Kere, J. et al., *Int. J. Pharm.* 182:33-39 (1999)), inclusion in cyclodextrins. This invention deploys a simple process involving spray drying of fenofibrate with mesoporous SBA-15 to produce stable amorphous fenofibrate and to improve its dissolution rate. Other poorly aqueous soluble model drugs, namely indomethacin, carbamazapine and ursodeoxycholic, are also spray-dried with mesoporous SBA-15 particles in order to improve their dissolution rate.

The formulation procedure is similar to Example 1. Typically, 1.0 g of the drug and 1.0 g of SBA-15 submicron particles were dispersed in 100 mL ethanol by stirring overnight. Spray drying is performed using Buchi 290B mini spray dryer. Dissolution rate analysis of spray-dried fenofibrate with mesoporous SBA-15 is performed using Varian VK7010 dissolution tester with UV online sampler and measurement system.

Figure 15:
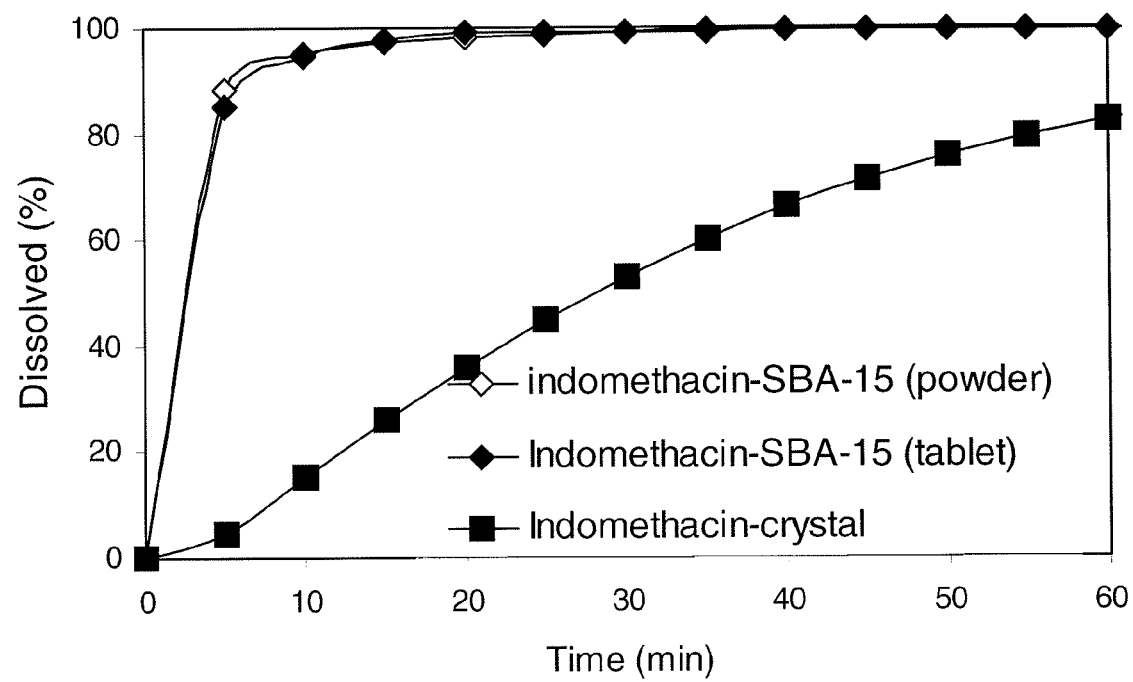
FIG. 15 illustrates dissolution profiles of spray-dried indomethacin with SBA-15 in powder form and tablet form, and a comparison with raw indomethacin crystal. (900 mL of pH 6.8 phosphate buffer, 50 mg spray-dried indomethacin with SBA-15 in powder form or tablet with 800 mg cornstarch at 1 ton press, raw crystal form is 25 mg).
Figure 16:
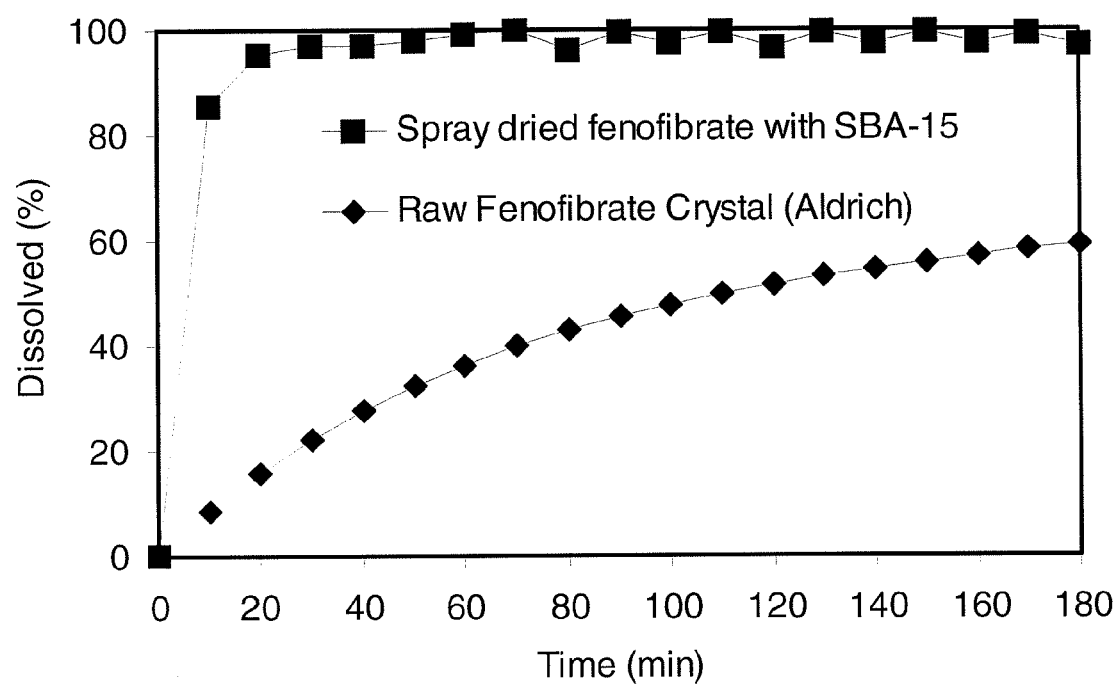
FIG. 16 illustrates a dissolution profile of spray-dried fenofibrate and compared with commercial fenofibrate. (dissolution medium: 900 mL of 0.1N HCl with 0.5% of Tween80; 20 mg of fenofibrate and equivalent active ingredient in spray-dried fenofibrate are tested at 30° C./100 rpm).

The dissolution rate of each of the spray-dried drugs with SBA-15 submicron particles is higher than commercial drug in the crystalline form. As shown in FIG. 15, spray-dried indomethacin reaches 97% of dissolution within 15 min, whereas commercial indomethacin has only reached 25%. The dissolution of spray-dried indomethacin is also performed both in tablet form and powder form. The tablet form exhibits almost same dissolution profile as that in powder form. As displayed in FIG. 16, the dissolution rate of spray-dried fenofibrate with mesoporous SBA-15 reaches 95% in 20 min, whereas only 15.6% of raw fenofibrate crystal is dissolved in the same time period.

Figure 17:
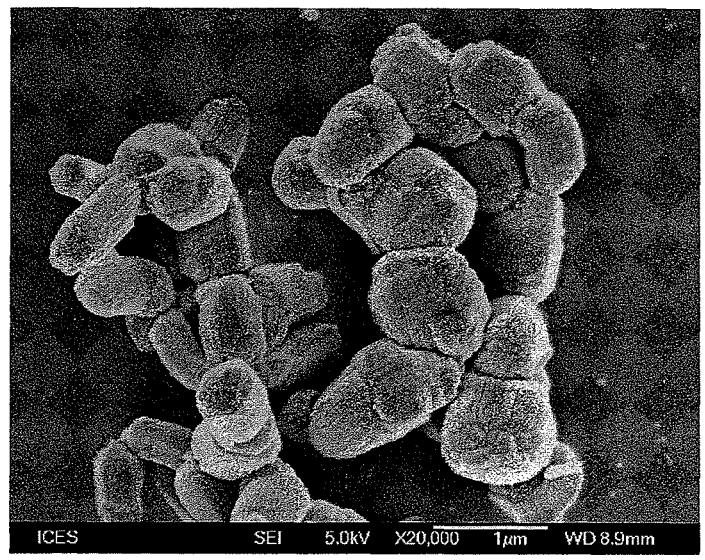
FIG. 17 illustrates a SEM image of spray-dried indomethacin/SBA-15 submicron particles.
Figure 18:
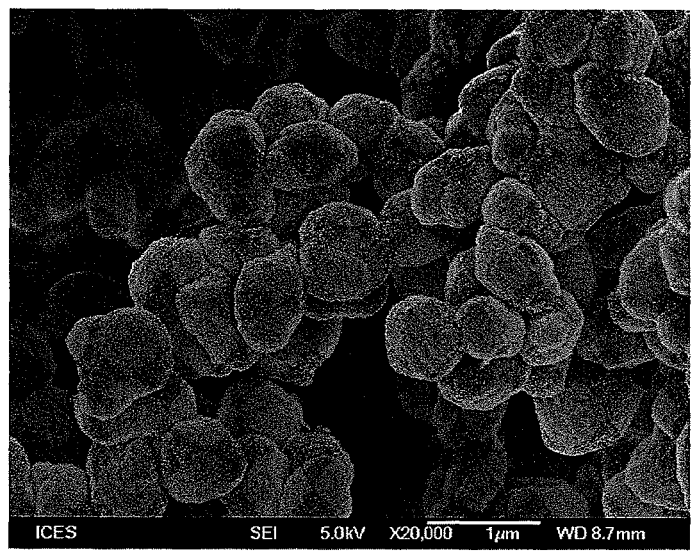
FIG. 18 depicts the SEM image of spray-dried carbamazapine/SBA-15 submicron particles.
Figure 19:
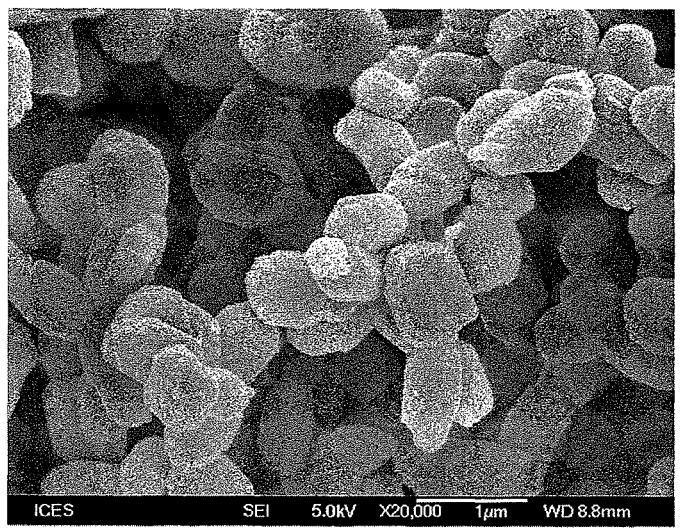
FIG. 19 illustrates a SEM image of spray-dried ursodeoxycholic/SBA-15 submicron particles.
Figure 20:
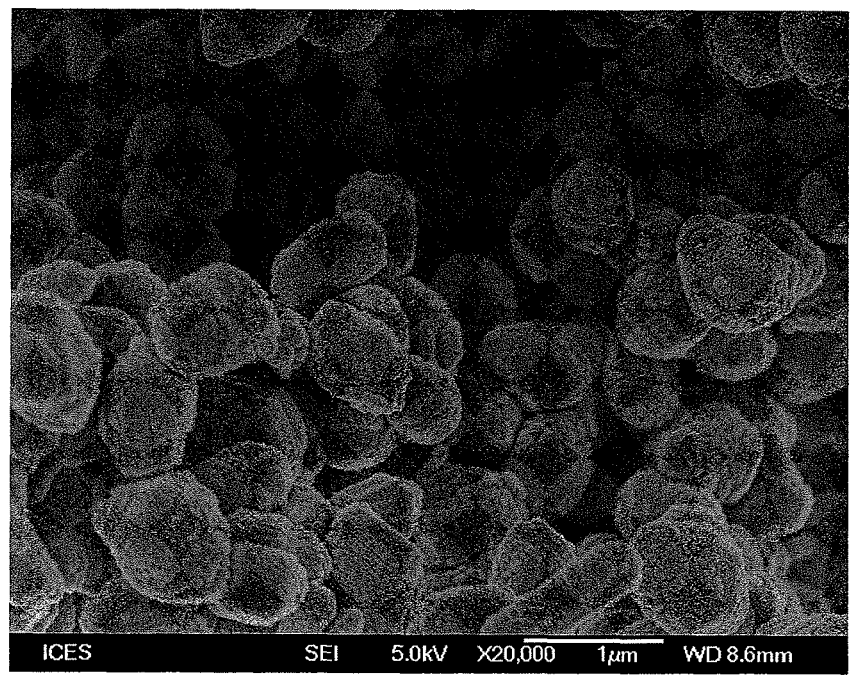
FIG. 20 illustrates a SEM image of spray-dried fenofibrate/SBA-15 submicron particles.

SEM investigation confirms that the morphology of spray-dried these poorly water soluble drugs, such as indomethacin (FIG. 17), carbamazapine (FIG. 18), ursodeoxycholic (FIG. 19), fenofibrate (FIG. 20), is not obviously changed as compared with the bare mesoporous particles. The result indicates that most of drug is entrapped inside the pore channels.

Figure 21:
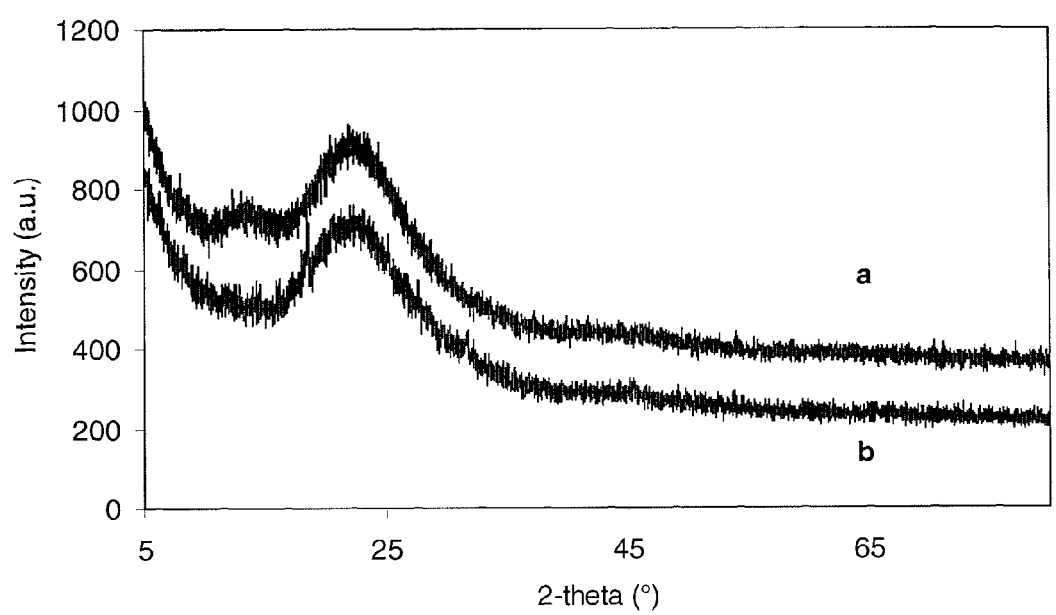
FIG. 21 illustrates a XRD pattern of co-spray-dried mesoporous SBA-15 submicron particles with (a) carbamazapine and (b) indomethacin after storage at 40° C./75% RH for one year.
Figure 22:
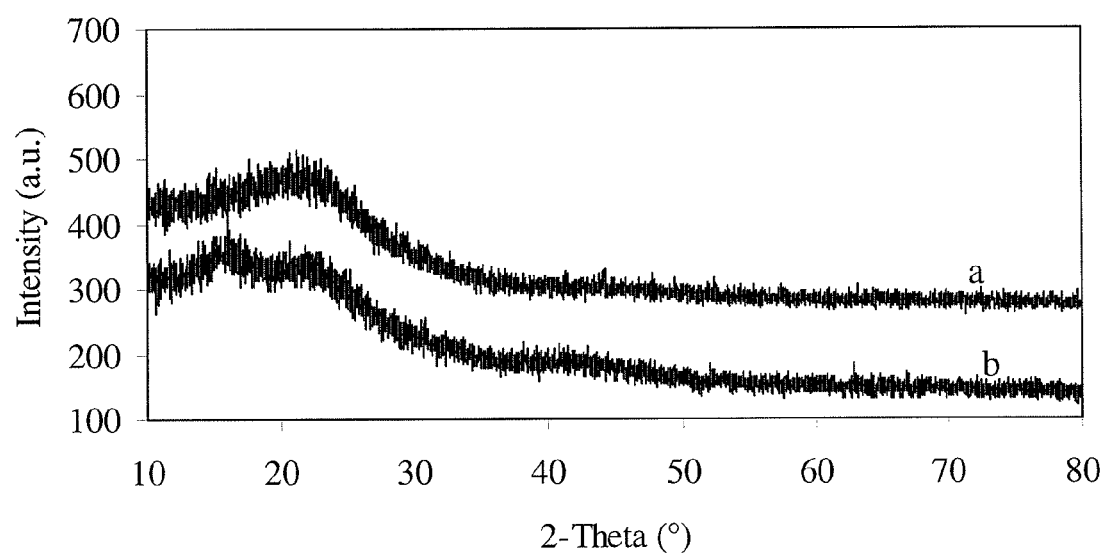
FIG. 22 illustrates a XRD pattern of co-spray-dried mesoporous SBA-15 submicron particles with (a) fenofibrate and (b) ursodeoxycholic after storage at 40° C./75% RH for six months.

The amorphous state of these drugs formed by spray drying with mesoporous materials is stable after being subject to stress conditions of 40° C./75% RH for at least six months. As shown in FIG. 21, both the spray-dried indomethacin and carbamazapine are stable in the amorphous form after storage at 40° C./75% RH for 12 months. The stability of spray-dried fenofibrate and ursodeoxycholic has been tested for six months so far and both showed stability in the amorphous form as illustrated in FIG. 22.

In comparison, amorphous indomethacin obtained from direct quench method is unstable and was re-crystallized after being tested at the same conditions for just one week. The amorphous stability of active ingredient formulated with mesoporous materials is attributed to the high pore volume and pore structures, which host active ingredients in nano-sized space in the amorphous state and the pore walls prevent re-crystallization under stress test conditions during storage.

Example 8

Mesoporous carbon is selected to host poorly aqueous soluble drugs. Mesoporous carbon is synthesized based on SBA-15 submicron particles as template. Sucrose was filled into pore channels of SBA-15 particles. Carbonization was performed at 900° C. in $N_2$ atmosphere. The template silica was removed by dissolving in 1N NaOH solution and followed by washing with de-ionized water. The mesoporous carbon was dried at 120° C. in air.

Figure 23:
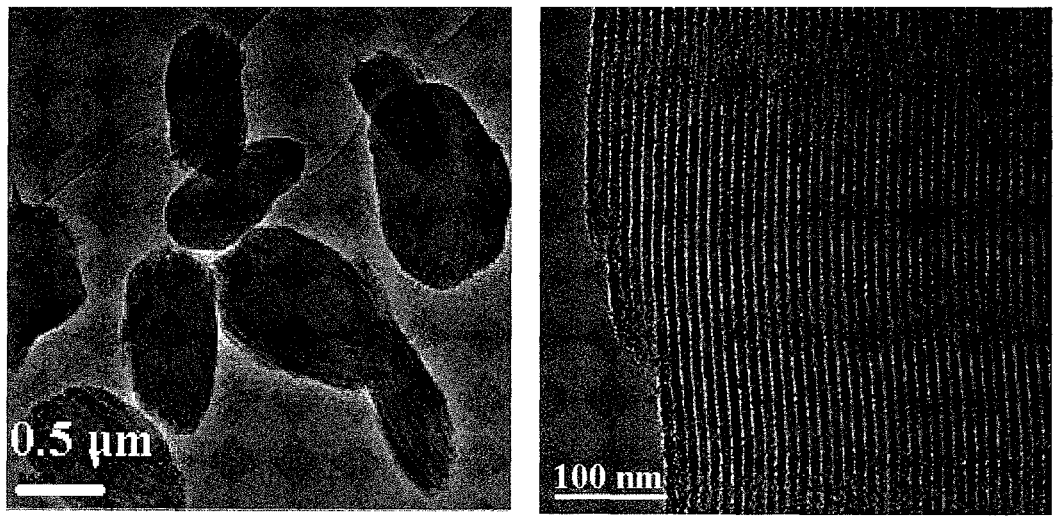
FIG. 23 illustrates TEM images of mesoporous carbon reveal their morphology and pore structure.
Figure 24:
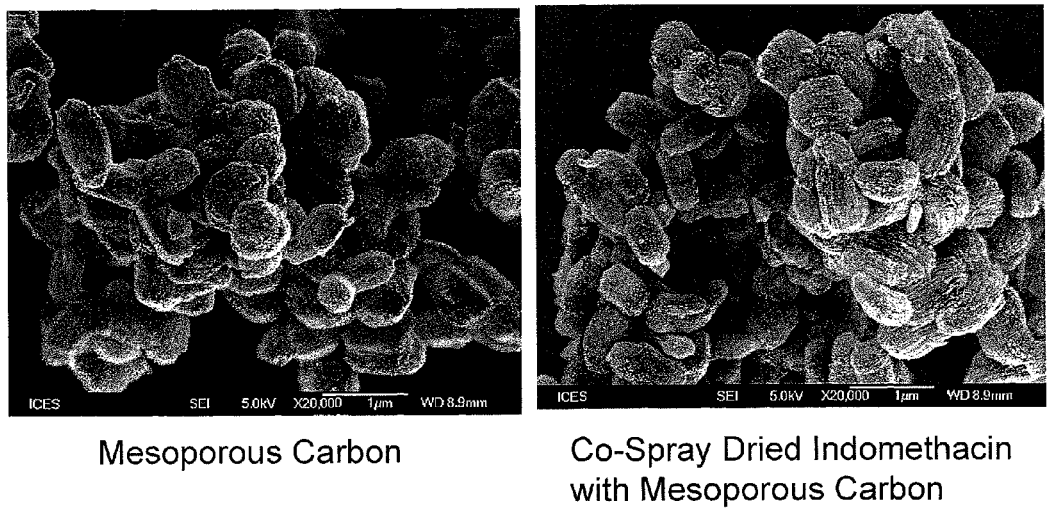
FIG. 24 illustrates SEM images of mesoporous carbon and co-sprayed indomethacin with mesoporous carbon (50:50 wt).

FIG. 23 displays the morphology and pore structure of mesoporous carbon. To formulate poorly aqueous soluble drugs, 0.5 g of mesoporous carbon and 0.5 g of indomethacin are dispersed in 50 mL ethanol by stirring overnight. Spray drying is performed in Buchi 290B mini spray drier. XRD measurement confirm that spray-dried indomethacin with mesoporous carbon (50:50 wt) is in the amorphous form. SEM measurement as shown in FIG. 24 confirms that the morphology of mesoporous carbon materials is not obviously changed. This indicates that most of the indomethacin is located inside the pore channels. Dissolution of spray-dried indomethacin with mesoporous carbon is performed in Varian VK7010 dissolution tester with UV online sampler and measurement system.

Figure 25:
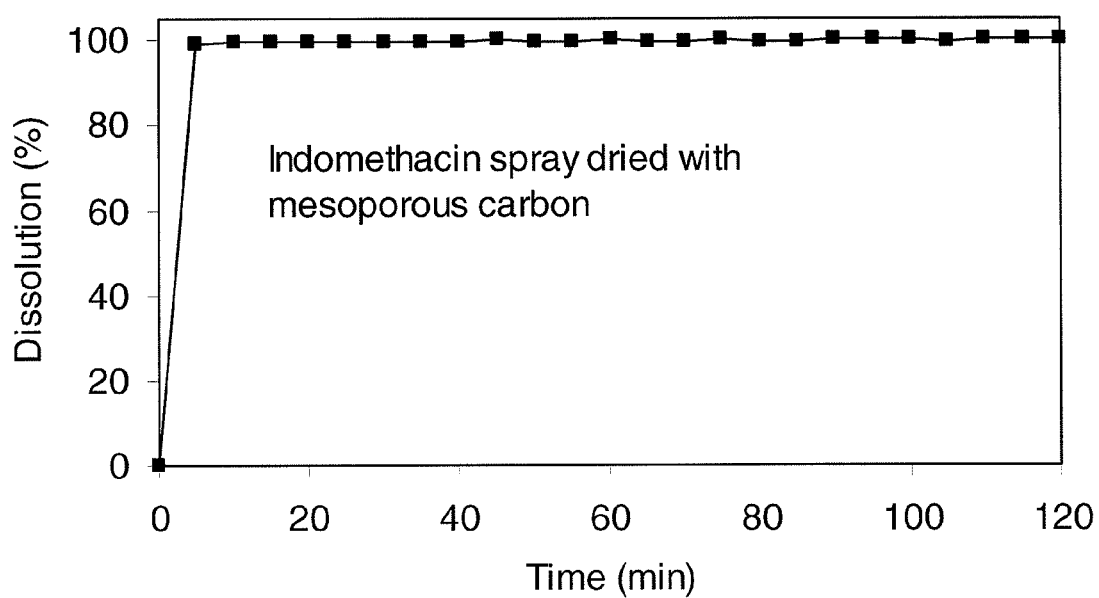
FIG. 25 illustrates a dissolution profile of powder form spray-dried indomethacin with mesoporous carbon. (medium: 900 mL of pH 6.8 phosphate buffer, 65 mg of spray-dried indomethacin with mesoporous carbon (50:50 wt. %), temperature 37° C., stirring rate 100 rpm).

FIG. 25 illustrates the dissolution profile of powder spray-dried indomethacin with mesoporous carbon in pH 6.8 buffer solution. It shows that spray drying of indomethacin with mesoporous carbon significantly enhances the dissolution rate of indomethacin, reaching 98% in 5 min. The immediate release of poorly soluble indomethacin is attributed to the amorphous form of active ingredient inside mesoporous carbon matrix.

Co-spray drying of poorly aqueous ingredients with mesoporous materials is a unique method to entrap these active ingredients in the amorphous form within the nanosized pore structure.

What is claimed is:

1. An orally administrable pharmaceutical composition, said pharmaceutical composition comprising:
   a substantially water-insoluble pharmaceutical active ingredient selected from the group consisting of ibuprofen, fenofibrate, indomethacin, carbamazepine, and ursodeoxycholic acid in a stable amorphous form which is present at about 50% w/w to about 75% w/w; and
   a mesoporous composition having a plurality of nanopores and selected from the group consisting of MCM-41, MCM-48, SBA-15, MCF, MSU and CMK-3, wherein said substantially water-insoluble pharmaceutical active ingredient is spray-dried together with said mesoporous composition to entrap said pharmaceutical active ingredient within said nanopores, wherein there is no crystal growth detected after 12 months storage at 40° C. and 75% relative humidity of said stable amorphous form.

2. The pharmaceutical composition of claim 1, wherein said substantially water-insoluble pharmaceutical active ingredient is present at about 50% w/w.

3. The pharmaceutical composition of claim 1, wherein said substantially water-insoluble pharmaceutical active ingredient is ibuprofen.

4. The pharmaceutical composition of claim 1, wherein said mesoporous composition has a particle size of about 0.1 μm to about 100 μm.

5. The pharmaceutical composition of claim 4, wherein said mesoporous composition has a particle size of about 0.3 μm to about 50 μm.

6. The pharmaceutical composition of claim 5, wherein said mesoporous composition has a particle size of about 0.5 μm to about 30 μm.

7. The pharmaceutical composition of claim 1, wherein said plurality of nanopores of said mesoporous composition have a mean diameter of about 1 nm to about 100 nm.

8. The pharmaceutical composition of claim 7, wherein said plurality of nanopores of said mesoporous composition have a mean diameter of about 1.5 nm to about 50 nm.

9. The pharmaceutical composition of claim 8, wherein said plurality of nanopores of said mesoporous composition have a mean diameter of about 2 mm to about 30 nm.

10. The pharmaceutical composition of claim 1, wherein said plurality of nanopores of said mesoporous composition have a mean volume of about 0.2 $cm^3/g$ to about 4.0 $cm^3/g$.

11. The pharmaceutical composition of claim 10, wherein said plurality of nanopores of said mesoporous composition have a mean volume of about 0.8 $cm^3/g$ to about 3.0 $cm^3/g$.

12. The pharmaceutical composition of claim 1, wherein said mesoporous composition comprises an oxide.

13. The pharmaceutical composition of claim 12, wherein said mesoporous composition comprises a silicate.

14. The pharmaceutical composition of claim 13 wherein said mesoporous composition is SBA-15.

15. The pharmaceutical composition of claim 1, wherein said pharmaceutical composition has an increased dissolution profile compared to the pharmaceutical composition without said mesoporous composition.

16. A method for preparing an orally administrable pharmaceutical composition comprising a substantially water-insoluble pharmaceutical active ingredient which is present at about 50% w/w to about 75% w/w and is selected from the group consisting of ibuprofen, fenofibrate, indomethacin, carbamazepine, and ursodeoxycholic acid, said method comprising:
   admixing said substantially water-insoluble pharmaceutical active ingredient with a mesoporous composition selected from the group consisting of MCM-41, MCM-48, SBA-15, MCF, MSU, and CMK-3 in a suitable solvent or mixture of solvents; and
   spray-drying said substantially water-insoluble pharmaceutical active ingredient with said mesoporous composition to entrap said pharmaceutical active ingredient within said nanopores as a stable amorphous solid.

17. The method of claim 16, wherein said substantially water-insoluble pharmaceutical active ingredient is ibuprofen.

18. The method of claim 16, wherein said mesoporous composition has a particle size of about 0.1 μm to about 100 μm.

19. The method of claim 18, wherein said mesoporous composition has a particle size of about 0.3 μm to about 50 μm.

20. The method of claim 19, wherein said mesoporous composition has a particle size of about 0.5 μm to about 30 μm.

21. The method of claim 16, wherein said plurality of nanopores of said mesoporous composition have a mean diameter of about 1 nm to about 100 nm.

22. The method of claim 21, wherein said plurality of nanopores of said mesoporous composition have a mean diameter of about 1.5 nm to about 50 nm.

23. The method of claim 22, wherein said plurality of nanopores of said mesoporous composition have a mean diameter of about 2 nm to about 30 nm.

24. The method of claim 16, wherein said plurality of nanopores of said mesoporous composition have a mean volume of about 0.2 $cm^3/g$ to about 4.0 $cm^3/g$.

25. The method of claim 24, wherein said plurality of nanopores of said mesoporous composition have a mean volume of about 0.8 $cm^3/g$ to about 3.0 $cm^3/g$.

26. The method of claim 16, wherein said mesoporous composition comprises an oxide.

27. The method of claim 26, wherein said mesoporous composition comprises a silicate.

28. The method of claim 27, wherein said mesoporous composition is SBA-15.

* * * * *